United States Patent [19]

Hartig et al.

[11] Patent Number: 5,041,682

[45] Date of Patent: Aug. 20, 1991

[54] WORKING UP REACTION MIXTURES CONTAINING CYCLOHEXANOL CYCLOHEXANONE AND CYCLOHEXYL HYDROPEROXIDE

[75] Inventors: Juergen Hartig, Gruenstadt; Armin Stoessel, Frankenthal; Ekhart Lucas, Wachenheim, all of Fed. Rep. of Germany

[73] Assignee: BASF Aktiengesellschaft, Ludwigshafen, Fed. Rep. of Germany

[21] Appl. No.: 245,975

[22] Filed: Sep. 19, 1988

Related U.S. Application Data

[63] Continuation of Ser. No. 842,996, Mar. 24, 1986, abandoned.

[30] Foreign Application Priority Data

Apr. 16, 1985 [DE] Fed. Rep. of Germany ....... 3513568

[51] Int. Cl.$^5$ .............................................. C07C 45/53
[52] U.S. Cl. .................... 568/342; 568/368; 568/835
[58] Field of Search ................. 568/342, 366, 835

[56] References Cited

U.S. PATENT DOCUMENTS

| 2,851,496 | 9/1958 | Cates et al. | 568/342 |
| 3,316,302 | 4/1967 | Steeman et al. | 568/366 |
| 3,557,215 | 1/1971 | Bonnart et al. | 260/586 |
| 3,917,708 | 11/1975 | Kuessner et al. | 260/586 |
| 3,927,108 | 12/1975 | van de Moesdijk | 568/342 |
| 3,937,735 | 2/1976 | Dols | 260/586 |
| 4,163,027 | 7/1979 | Magnaussen et al. | 568/366 |
| 4,250,118 | 2/1981 | van de Mond et al. | 568/366 |

FOREIGN PATENT DOCUMENTS

| 701187 | 1/1965 | Canada | 568/366 |
| 0092867 | 2/1983 | European Pat. Off. | 568/342 |
| 1211629 | 3/1966 | Fed. Rep. of Germany | 568/342 |
| 545758 | 2/1974 | Switzerland | 568/342 |
| 1133257 | 1/1985 | U.S.S.R. | 568/366 |
| 909227 | 10/1962 | United Kingdom | 568/333 |
| 1032035 | 6/1966 | United Kingdom | 568/366 |
| 1190002 | 4/1970 | United Kingdom | 568/333 |
| 1382849 | 2/1975 | United Kingdom | 568/308 |

*Primary Examiner*—James H. Reamer
*Attorney, Agent, or Firm*—Keil & Weinkauf

[57] ABSTRACT

Reaction mixtures which contain cyclohexanol, cyclohexanone and cyclohexyl hydroperoxide and are obtained in the oxidation of cyclohexane with molecular oxygen, or with a gas containing this, in the liquid phase are worked up by a process in which the reaction mixture is hydrogenated in the presence of a noble metal catalyst at elevated temperatures and under superatmospheric pressure, the resulting mixture is treated with an aqueous alkali metal carbonate solution, and cyclohexanol and cyclohexanone are separated off by distillation.

3 Claims, No Drawings

WORKING UP REACTION MIXTURES CONTAINING CYCLOHEXANOL CYCLOHEXANONE AND CYCLOHEXYL HYDROPEROXIDE

EP-A-92 867 discloses that oxidation mixtures containing cyclohexanol, cyclohexanone and cyclohexyl hydroperoxide and obtained from the oxidation of cyclohexane are treated with an aqueous solution of an alkali metal hydroxide in the presence of a catalytic metal salt in order to convert the cyclohexyl hydroperoxide present in the reaction mixture into cyclohexanol and cyclohexanone. This process has the disadvantages that substantial amounts of alkali metal hydroxides have to be used and furthermore considerable amounts of cyclohexanone are lost, with the formation of high boilers.

In another process, disclosed in Swiss Patent 545,758, reaction mixtures containing cyclohexanol, cyclohexanone and cyclohexyl hydroperoxide and obtained in the oxidation of cyclohexane are first hydrogenated in the presence of a noble metal catalyst, and the resulting hydrogenation mixture is then treated with an aqueous alkali metal solution. This process too results in the formation of as much as 2.7% by weight of high-boiling by-products.

It is an object of the present invention to provide a process for working up reaction mixture$ which contain cyclohexanol, cyclohexanone and cyclohexyl hydroperoxide and are obtained in the oxidation of cyclohexane, the said process producing smaller amounts of waste liquors than hitherto and in particular resulting in the formation of a smaller amount of high-boiling by-products.

We have found that this object is achieved by a process for working up reaction mixtures which contain cyclohexanol, cyclohexanone and cyclohexyl hydroperoxide and are obtained in the oxidation of cyclohexane with molecular oxygen, or a gas containing this, in the liquid phase, in which the reaction mixture is hydrogenated in the presence of a noble metal catalyst at elevated temperatures and under superatmospheric pressure, the resulting mixture is treated with an aqueous alkaline solution, the aqueous phase is separated off, and cyclohexanol and cyclohexanone are removed by distillation, wherein an aqueous alkali metal carbonate solution is used.

The novel process has the advantages that the amount of waste liquors requiring treatment is reduced, as is the amount of high-boiling by-products obtained.

According to the invention, the starting materials used are reaction mixtures obtained by oxidation of cyclohexane with molecular oxygen, or with a gas containing this, e.g. air, in the liquid phase. In this procedure, it is advantageous to maintain a temperature of from 130° to 200° C. and a pressure of from 5 to 25 bar. If necessary, catalysts, such as cobalt salts, may also be used. Typical reaction mixtures contain, in addition to cyclohexane, from 3 to 7% by weight of cyclohexanone and cyclohexanol and from 0.5 to 3.5% by weight of cyclohexyl hydroperoxide, as well as by-products such as esters, carboxylic acids and, possibly, up to 2% by weight of water. Suitable reaction mixtures are obtained, for example, by the process described in German Patent 1,046,610. Advantageously, the reaction mixtures thus obtained are washed with water and/or an aqueous alkali metal carbonate solution before being treated further.

The reaction mixture is hydrogenated in the presence of a noble metal catalyst at elevated temperatures and under superatmospheric pressure, advantageously at from 80° to 160° C., in particular from 100° to 140°) C., and preferably under from 3 to 20, in particular from 5 to 15, bar.

Examples of suitable noble metal catalysts are the metals palladium, platinum, rhodium and ruthenium, palladium being particularly preferred. The catalytically active metals are advantageously deposited on carriers, such as carbon, kieselguhr, silica gel or alumina, and used in this form. Such supported catalysts advantageously contain from 0.1 to 1.0% by weight of the stated noble metals. A particularly preferred catalyst is palladium on $\gamma$-alumina.

After the hydrogen has been removed, the resulting hydrogenated mixture which, in addition to cyclohexane, contains cyclohexanol and cyclohexanone as well as by-products, such as carboxylic acids and esters, is treated with an aqueous solution of an alkali metal carbonate, e.g. sodium carbonate or potassium carbonate. Potassium carbonate has proven particularly useful. Advantageously, from 0.05 to 1.0 mole of alkali metal carbonate in the form of a 5–50% strength by weight aqueous solution is used per part by weight of hydrogenated reaction mixture. The treatment is carried out as a rule at from 80° to 140° C. and under from 5 to 20 bar. The treatment is effected with thorough mixing of the phases, for example in a mixing tube, a residence time of from 2 to 20 minutes preferably being maintained. The aqueous alkali metal carbonate solution is then separated off from the hydrogenation mixture treated in this manner by a conventional separation method, for example decantation. The resulting aqueous waste liquor is advantageously used for the treatment of the reaction mixture from the oxidation of cyclohexane, before the hydrogenation stage.

The hydrogenation mixture treated in this manner is worked up by distillation; the cyclohexane recovered is recycled to the cyclohexane oxidation and cyclohexanol and cyclohexanone are obtained, these in turn being separated by distillation.

Where the desired end product is cyclohexanone, the cyclohexanol obtained is dehydrogenated in the presence of a zinc oxide catalyst at from 320° to 390° C. in the gas phase. A suitable process is described in, for example, German Published Application DAS 1,211,629.

The hydrogen obtained in this procedure is advantageously used for the hydrogenation of the reaction mixture from the oxidation of cyclohexane, as described above.

In order to reduce the amount of waste liquors which have to be disposed of, it has proven useful to incinerate the aqueous alkali metal carbonate solutions, if appropriate together with other wash waters and high boilers, and to recover alkali metal carbonate, which is reused for the alkali treatment, in the form of an aqueous alkali metal carbonate solution.

The desired substances cyclohexanol and cyclohexanone produced by the process of the invention are important starting materials for fiber raw materials such as adipic acid and caprolactam.

Examples which follow illustrate the invention.

EXAMPLE 1

145 kg/hour of cyclohexane and 10.0 m³ (S.T.P)/hour of air are passed into a reaction tower provided with baffles. The reaction is carried out at 170° C. and under 17 bar, the resulting reaction mixture is washed with 4 l/hour of water at 100° C. and the aqueous phase is separated off. The reaction mixture thus obtained contains, in addition to cyclohexane, 1.45% by weight of cyclohexanol, 0.55% by weight of cyclohexanone, 3.1% by weight of cyclohexyl hydroperoxide and small amounts of carboxylic acids and carboxylates.

Thereafter, the reaction mixture, together with an aqueous potassium carbonate solution which is about 50% strength by weight and is obtained as a waste liquor in the alkali treatment after the hydrogenation, is passed through a mixing zone, the aqueous phase is separated off and the mixture is then washed with 0.5 l/hour of water in order to remove potassium salts. The reaction mixture pretreated in this manner is passed from below into a reactor which has a diameter of 20 cm and a height of 1.2 m and is charged with γ-alumina extrudates containing 0.25% by weight of palladium. At the same time, 5 m³ (S.T.P.)/hour of hydrogen is fed in from below. The hydrogenation is carried out at 120° C. and under 8 bar, and cyclohexyl hydroperoxide is completely converted to cyclohexanol and also to cyclohexanone. Hydrogen fed in over and above the stoichiometric amount is separated off in a downstream separator and reused for the hydrogenation. The water of reaction obtained in the hydrogenation is likewise removed in the separator, and used as wash water after the alkali treatment. The hydrogenated reaction mixture is then treated with 1.5 kg/hour of 50% strength by weight aqueous potassium carbonate solution in a mixing zone at 120° C., the residence time being 10 minutes. The aqueous potassium carbonate solution is then separated off and reused in the alkali washes for the crude oxidation products prior to hydrogenation. The potassium salts are removed by washing again with water. Cyclohexane is isolated by distillation in a column and is reused in the oxidation of cyclohexane, and cyclohexanol and cyclohexanone are obtained as end products. A mixture of 76.5% by weight of cyclohexanol, 21.0% by weight of cyclohexanone, 1.5% by weight of low boilers and 1.0% by weight of high boilers is obtained. The yield of cyclohexanone and cyclohexanol is 84.5 mol%, based on a cyclohexane conversion of 4.60%.

The cyclohexanol which remains after the cyclohexanone has been separated off by distillation is dehydrogenated in the presence of a zinc oxide catalyst at 365° C. in the gas phase. The hydrogen obtained in this procedure is used for hydrogenating the reaction mixture from the oxidation of cyclohexane.

EXAMPLE 2

145 kg/hour of cyclohexane and 10.0 m³ (S.T.P)/hour of air are passed into a reaction tower provided with baffles. The reaction is carried out at 176° C. and under 4.8 bar, the resulting reaction mixture is washed with 4 l/hour of water at 90° C. and the aqueous phase is separated off. The reaction mixture thus obtained contains, in addition to cyclohexane, 1.5% by weight of cyclohexanol, 0.55% by weight of cyclohexanone, 3.1% by weight of cyclohexyl hydroperoxide and small amounts of carboxylic acids and carboxylates.

Thereafter, the reaction mixture, together with an aqueous sodium carbonate solution which is about in the alkali treatment after the hydrogenation, is passed through a mixing zone, the aqueous phase is separated off and the mixture is then washed with 0.5 l/hour of water in order to remove the sodium salts. The reaction mixture pretreated in this manner is passed from below into a reactor which has a diameter of 20 cm and a height of 1.2 m and is charged with γ-alumina extrudates containing 0.25% by weight of palladium. At the same time, 3 m³ (S.T.P.)/hour of hydrogen is fed in from below. The hydrogenation is carried out at 100° C. and under 6.8 bar, and cyclohexyl hydroperoxide is completely converted to cyclohexanol and also to cyclohexanone. Hydrogen fed in over and above the stoichiometric amount is separated off in a downstream separator and reused for the hydrogenation. The water of reaction obtained in the hydrogenation is likewise removed in the separator, and used as wash water after the alkali treatment. The hydrogenated reaction mixture is then treated with 8 kg/hour of 16% strength by weight aqueous sodium carbonate solution in a mixing zone at 125° C., the residence time being 10 minutes. The aqueous sodium carbonate solution is then separated off and reused in the alkali washes for the crude oxidation products prior to hydrogenation. The sodium salts are removed by washing again with water. Cyclohexane is isolated by distillation in a column and is reused in the oxidation of cyclohexane, and cyclohexanol and cyclohexanone are obtained as end products. A mixture of 79.0% by weight of cyclohexanol, 18.5% by weight of cyclohexanone, 1.2% by weight of low boilers and 1.3% by weight of high boilers is obtained. The yield of cyclohexanone and cyclohexanol is 84 mol%, based on a cyclohexane conversion of 4.7%.

The cyclohexanol which remains after the cyclohexanone has been separated off by distillation is dehydrogenated in the presence of a zinc oxide catalyst at 365° C. in the gas phase. The hydrogen obtained in this procedure is used for hydrogenating the reaction mixture from the oxidation of cyclohexane.

We claim:

1. A process for working up a reaction mixture which contains cyclohexanol, cyclohexanone and cyclohexyl hydroperoxide and has been obtained in the oxidation of cyclohexane with molecular oxygen, or with a gas containing molecular oxygen, in the liquid phase which process comprises:
   (a) hydrogenating the reaction mixture in the presence of a noble metal catalyst at elevated temperatures and under superatmospheric pressure;
   (b) treating the resulting mixture at a temperature from 50° to 140° C. with 0.05 to 1.0 mole of alkali metal carbonate in the form of a 5 to 50% strength by weight aqueous solution;
   (c) separating the aqueous alkali metal carbonate solution from the hydrogenation mixture;
   (d) incinerating the separated aqueous alkali metal carbonate solution and recovering the alkali metal carbonate which is reused in form of an aqueous solution in step (b), and
   (e) separating cyclohexanol and cyclohexanone from the hydrogenation mixture by distillation.

2. The process of claim 1, wherein the alkali metal carbonate is potassium carbonate.

3. The process of claim 1, wherein cyclohexanol is dehydrogenated in the presence of a zinc oxide catalyst at from 320° to 390° C. in the gas phase to give cyclohexanone, and the hydrogen obtained in this procedure is used for hydrogenating the reaction mixture from the oxidation of cyclohexane.

* * * * *